United States Patent [19]

Disdier et al.

[11] 4,387,246
[45] Jun. 7, 1983

[54] METHOD OF PREPARING ORTHOTRIFLUOROMETHYL ANILINE

[75] Inventors: Camille Disdier, Villeurbanne; Jacques-Pierre Martinaud, Lyons, both of France; John W. Sullivan, Jr., Neshanic Station, N.J.

[73] Assignee: Rhone-Poulenc Industries, Paris, France

[21] Appl. No.: 328,067

[22] Filed: Dec. 7, 1981

[30] Foreign Application Priority Data

Dec. 12, 1980 [FR] France .............................. 80 26367

[51] Int. Cl.³ ............................................. C07C 87/48
[52] U.S. Cl. .................................................. 564/417
[58] Field of Search ......................................... 564/417

[56] References Cited

U.S. PATENT DOCUMENTS

| | | | |
|---|---|---|---|
| 2,056,899 | 10/1936 | Hoffa et al. ...................... | 564/417 X |
| 3,328,465 | 6/1967 | Spiegler .......................... | 564/417 X |
| 3,471,563 | 10/1969 | Brake ............................. | 564/417 UX |
| 3,499,034 | 3/1970 | Gonzalez .......................... | 564/417 |
| 4,195,037 | 3/1980 | Harada et al. .................... | 564/417 X |

FOREIGN PATENT DOCUMENTS

| | | |
|---|---|---|
| 38465 | 10/1981 | European Pat. Off. . |
| 39810 | 11/1981 | European Pat. Off. . |
| 637318 | 10/1936 | Fed. Rep. of Germany . |
| 1593265 | 1/1971 | Fed. Rep. of Germany . |
| 62645 | 8/1971 | Luxembourg . |

OTHER PUBLICATIONS

*Chem. Abs.* 8194e (1954).
*Chem. Abs.* 4430b (1960).
*J. Org. Chem.*, vol. 24, 294, 421 (1959).
*J. Org. Chem.*, vol. 28, 2332 (1963).
*Chem. Ber.*, vol. 95, 523, 528 (1962).
*Chem. Ind.* (London), 1348 (1959).
*Bull. Soc. Chim.* (France), 2442 (1963).

*Primary Examiner*—Paul F. Shaver

[57] ABSTRACT

A process for preparing orthotrifluoromethyl aniline from trifluoromethyl benzene is disclosed. The steps are (a) reacting the trifluoromethyl benzene with gaseous chlorine in the presence of a chlorination catalyst until at least 90% of the trifluoromethyl benzene is consumed; (b) nitrating the crude mixture from step (a) using a mixture of sulfuric acid and nitric acid until disappearance of the chlorotrifluoromethyl benzenes; (c) settling and washing the organic phase from step (b); (d) subjecting the organic phase from step (c) to a first hydrogenation under pressure in the presence of a hydrogenation catalyst consisting of Raney nickel and/or Raney nickel doped with chromium, in an organic-solvent medium until complete disappearance of the chloronitrotrifluoromethyl benzenes; (e) subjecting the mixture from step (d) to a second hydrogenation in the presence of an additional amount of Raney nickel and in the presence of at least one alkaline base; and (f) removing the orthotrifluoromethyl aniline by distillation from the reaction mixture.

15 Claims, No Drawings

METHOD OF PREPARING ORTHOTRIFLUOROMETHYL ANILINE

BACKGROUND OF THE INVENTION

The present invention relates to a method of preparing orthotrifluoromethyl aniline from trifluoromethyl benzene. Orthotrifluoromethyl aniline is industrially important because it is used as an intermediate in the synthesis of dyestuffs.

Kemichi Fukui et al. (Chemical Abstracts 1960 4430 b) describe the nitration of trifluoromethyl benzene to obtain metanitrotrifluoromethyl benzene, which is converted into metatrifluoromethyl aniline. The acetylation of the aniline compound by acetic acid gives metaacetylaminotrifluoromethyl benzene, the nitration of which yields 2-nitro-5-acetyl-aminotrifluoromethyl benzene.

The latter, by hydrolysis, gives 2-nitro-5-amino-trifluoromethyl benzene. The elimination of the amine group is effected by reductive diazotation, which makes it possible to obtain orthonitrotrifluoromethyl benzene, the reduction of which leads to orthotrifluoromethyl aniline.

The main drawback of this method is its length. Seven steps (not including separation and purification steps) are necessary to obtain the desired product from the trifluoromethyl benzene starting material. Furthermore, as is well known, diazotation is a difficult procedure. In addition, purification operations are necessary after most of the steps. Finally, yields are limited.

L. M. Yagupolsky and N. I. Manko (Chemical Abstracts 1954 8194 e) disclose treating orthotrifluoromethyl benzamide with sodium hypobromite in accordance with the Hoffman degradation reaction. One drawback of this reaction is the well known possibility of forming N-bromoamines, which are explosive. Furthermore, the raw material used in this process is not readily available industrially.

SUMMARY OF THE INVENTION

The present invention avoids the above-described disadvantages and provides a safe method of making orthotrifluoromethyl aniline. Broadly, the method is as follows. Trifluoromethyl benzene is reacted with gaseous chlorine in the presence of a chlorination catalyst until at least 90% of the trifluoromethyl benzene has been consumed. The resultant crude mixture is nitrated by a mixture of sulfuric acid and nitric acid until the chlorotrifluoromethyl benzenes previously formed disappear. After settling of and washing the organic phase, it is subjected to two-stage hydrogenation. First, hydrogenation is carried out under pressure in the presence of a hydrogenation catalyst consisting of Raney nickel and/or Raney nickel doped with chromium, in organic solvent until complete disappearance of the chloronitrotrifluoromethyl benzenes present. The second hydrogenation is carried out in the presence of an additional amount of Raney nickel and in the presence of at least one alkaline base. Finally, the orthotrifluoromethyl aniline is separated by distillation from the crude reaction mixture.

The ease of obtaining orthotrifluoromethyl aniline by the present process is very surprising, for the following reasons. The nearly complete chlorination of trifluoromethyl benzene leads, as is known, to a mixture of monochloro and dichloro derivatives. In addition to the metachlorotrifluoromethyl benzene obtained in preponderant proportion and the para and ortho derivatives, isomers of dichlorotrifluoromethyl benzenes may be present in amounts of up to 20 to 25%.

This large proportion of dichloro products would lead one skilled in the art to either remove them or minimize their formation. The former involves distillation operations, which complicate the technique and increase the cost of manufacture. In the latter case, it is necessary to decrease the rate of conversion of the trifluoromethyl benzene and, therefore, to introduce a distillation step after the chlorination to remove the unreacted trifluoromethyl benzene. Either way, such a process would seem to present serious drawbacks.

However, contrary to the expectations of one skilled in the art, applicants have discovered that the dichloro compounds obtained at the end of the first step are advantageous because in the rest of the process they favor the formation of orthotrifluoromethyl aniline, the desired product. In other words, the step which one skilled in the art would have expected to be the greatest obstacle to the adoption of such a method has been discovered by applicants to be a step which favors the process technically and economically. In fact, with this process the yield is increased and the process simplified due to the absence of intermediate distillations.

More specifically, applicants have found that nitration of the dichloro products can be carried out under the same conditions as for the monochloro derivatives. Furthermore, applicants have discovered that the reduction and hydrodechlorination of the nitrodichloro derivatives can be carried out under relatively mild conditions, a fact that had not been established previously.

DETAILED DESCRIPTION OF THE INVENTION

In accordance with one preferred embodiment of the invention, for the first step, the chlorination catalyst is selected from the group consisting of ferric chloride, antimony pentachloride and the metals, iron and antimony, which are capable of producing in situ these two compounds. These may be used alone or in combination. Antimony pentachloride and ferric chloride are preferred.

The catalyst concentration is usually from about 0.1% to about 10% by weight, based on the trifluoromethyl benzene employed. Preferably, this percentage is from about 0.5 to about 5%.

Chlorination is generally carried out without solvent, although an organic solvent may be used. Chlorination is effected at a temperature from about 0° to about 100° C. and preferably from about 10° to about 80° C. Atmospheric pressure is preferred although pressures higher or lower than atmospheric pressure are still within the scope of the invention. Conversion of the trifluoromethyl benzene is preferably greater than 95% and may reach 100%.

For the nitration (second) step, solvent is not usually employed although the use of solvent is not excluded from the scope of the invention. The acids, $HNO_3$ and $H_2SO_4$, are used in such amounts that the weight ratio of the sulfuric acid to the chlorotrifluoromethyl benzenes initially present in the reaction medium is from about 0.5/1 to about 5/1 and preferably from about 0.7/1 to about 2/1 and the weight ratio of nitric acid to the chlorotrifluoromethyl benzenes initially present is from about 0.5/1 to about 5/1 and preferably from about 0.7/1 to about 2/1.

Nitration is effected at a temperature of from about 0° to about 80° C. and preferably from about 10° to about 60° C. Atmospheric pressure is preferred although other pressures are still within the scope of the invention. Decanting and washing the organic phase (third step) after the nitration reaction can be effected with water and caustic soda.

In accordance with a preferred embodiment of the invention, the first hydrogenation (fourth step) is carried out under a hydrogen pressure of from about 10 to about 50 bars and preferably from about 10 to about 30 bars. The temperature is from about 20° to about 100° C. and preferably from about 40° to about 80° C. The solvent is selected from the group consisting of methanol, ethanol, and propanol, with methanol being preferred.

This first hydrogenation is carried out in the presence of Raney nickel and/or Raney nickel doped with chromium as a hydrogenation catalyst. Raney nickel doped with chromium means Raney nickel containing from about 0.5 to about 5% by weight of chromium. The catalyst is used in such amount that its concentration is from about 3 to about 10% by weight based on the chloronitrotrifluoromethyl benzenes present. Preferably, this percentage is from about 4 to about 8%.

The second hydrogenation (fifth step) is carried out with the same temperature, hydrogen pressure, and solvent as the first hydrogenation. At least one mole of alkali base per mole of chlorotrifluoromethyl benzene initially present is introduced into the reaction medium for the second hydrogenation. Caustic soda or caustic potash is used as the alkali base, with caustic soda preferred.

During the second hydrogenation, from about 8 to about 20% by weight of Raney nickel based on the chloronitrotrifluoromethyl benzenes initially present is also introduced in one or more additions. Preferably, this percentage is from about 9 to about 15%.

Other characteristics and advantages of the present invention will become more evident from the following examples, which are in no way to be considered as constituting a limitation on the invention.

EXAMPLE 1

Twenty-nine and two-tenths kg of trifluoromethyl benzene and 292 g of antimony pentachloride are introduced into a reactor which is equipped with an agitator, a gas injector, and a hydrochloric-acid absorber. Gaseous chlorine at 20° C. is then introduced for 8 hours. After washing with water, 35.340 kg of mixture is obtained with the following vapor-phase chromatographic analysis:

| | |
|---|---|
| trifluoromethyl benzene: | 4% |
| metachlorotrifluoromethyl benzene: | 70.6% |
| parachlorotrifluoromethyl benzene: | 5.8% |
| orthochlorotrifluoromethyl benzene: | 3% |
| dichlorotrifluoromethyl benzenes (three isomers): | 16.6% |

Conversion of the trifluoromethyl benzene is 95% and the overall yield is 96%.

Fifteen and ninety-four hundredths kg of concentrated sulfuric acid (97%) and 15.940 kg of fuming nitric acid are introduced into an agitated reactor. This acid mixture is cooled to 10° C. and then 18.05 kg of the previously obtained crude mixture of trifluoromethyl benzene, chlorotrifluoromethyl benzenes, and dichlorotrifluoromethyl benzenes are added with agitation over the course of one hour while maintaining this temperature.

When the addition has been completed, the mixture is brought to 50° C. and held at that temperature for 6 hours. The organic phase is poured off and washed with water, with 10% caustic soda, and then again with water. In this way, 21.62 kg of a mixture is obtained with the following vapor-phase chromatographic analysis:

| | |
|---|---|
| chlorotrifluoromethyl benzene: | none detectable |
| nitrotrifluoromethyl benzene: | 3.9% |
| chloronitrotrifluoromethyl benzenes (four isomers): | 82.2% |
| dichloronitrotrifluoromethyl benzenes (four isomers): | 13.9% |

Conversion of the chlorotrifluoromethyl benzenes is 100% and the overall yield is 96%.

One and four-tenths liters of methanol and 50 g of Raney nickel are put into an agitated autoclave. This mixture is placed under 20 bars of hydrogen at 20° C. and agitated for 15 minutes. One and forty-six hundredths liters of methanol and 1 kg of the organic phase that was previously obtained are then added. Hydrogenation is effected at 80° C. under 20 bars. At the end of 1.5 hours, analysis by vapor-phase chromatography reveals that all of the chloronitrotrifluoromethyl benzenes have been consumed. The mixture is cooled to 50° C. and 622 g of 30.8% caustic soda is added. The mixture is then agitated for 15 minutes under 20 bars of hydrogen.

Fifty g of Raney nickel are then added and a second hydrogenation is effected under 20 bars of hydrogen at 50° C. for two hours. A further 50 g of Raney nickel are added and the hydrogenation is continued for an 2 hours more. The reaction is then complete. After filtration, concentration, and washing with water, 684 g of a mixture of amines is obtained having the following composition:

| | |
|---|---|
| orthotrifluoromethyl aniline: | 77.2% |
| metatrifluoromethyl aniline: | 20.5% |
| paratrifluoromethyl aniline: | 2.3% |

This mixture is subjected to distillation in a 20-plate column with a reflux ratio of 29/1 under an overhead pressure of 50 mm Hg. A total of 522 g of orthotrifluoromethyl aniline are obtained at a concentration of more than 99% corresponding to a yield of 99%.

EXAMPLE 2

Seven and three-tenths kg of trifluoromethyl benzene, 41 g of ferric chloride, and 20 g of iron are introduced into the reactor of Example 1. Chlorine is then added as in Example 1 at 20° C. for six hours. After washing with water, 9160 g of a mixture is obtained having the following analysis by vapor-phase chromatography:

| | |
|---|---|
| trifluoromethyl benzene: | 1.7% |
| metachlorotrifluoromethyl | |

-continued

| | |
|---|---|
| benzene: | 66.4% |
| parachlorotrifluoromethyl benzene: | 6.1% |
| orthochlorotrifluoromethyl benzene: | 2.6% |
| dichlorotrifluoromethyl benzenes: | 24.3% |

Conversion of the trifluoromethyl benzene is 98% and the overall yield is 98%.

Two thousand seven hundred fifty-three g of the above crude mixture are added to an agitated reactor. The mixture is cooled to 10° C. and a mixture of fuming nitric acid (1700 g) and concentrated (97%) sulfuric acid (2350 g) is added under agitation at this temperature over the course of one hour. The mixture is then held at 80° C. for six hours. The organic phase is poured off and washed with water, 10% caustic soda, and then again with water. In this way, 3290 g of a mixture are obtained with the following composition:

| | |
|---|---|
| chlorotrifluoromethyl benzene: | none detectable |
| nitrotrifluoromethyl benzene: | 1.8% |
| chloronitrotrifluoromethyl benzenes: | 74.8% |
| dichloronitrotrifluoromethyl benzenes: | 23.4% |

Conversion of the chlorotrifluoromethyl benzenes is 100% and the overall yield is 96%.

Twenty-nine hundred ml of methanol and 50 g of Raney nickel doped with chromium are added to an agitated autoclave. The pressure is brought to 12 bars of hydrogen at 50° C. with agitation for 15 minutes. One thousand g of the nitration product previously obtained are added under these conditions during 1.75 hours. The mixture is then maintained at 50° C. under 12 bars of hydrogen with agitation for an additional 1.5 hours. By this time, all of the chloronitrotrifluoromethyl benzenes have been consumed.

Six hundred thirty g of 31.1% caustic soda are then added and agitation is carried out at 50° C. and 12 bars of hydrogen for 15 minutes. Fifty g of Raney nickel are added and hydrogenation is effected for 2 hours at 50° C. under 12 bars of hydrogen. Another 50 g of Raney nickel are added and hydrogenation is continued for 3 hours under the same conditions. The reaction is then complete.

After filtration, concentration, and washing with water, 670 g of a mixture are obtained with the following composition:

| | |
|---|---|
| orthotrifluoromethyl aniline: | 76.7% |
| metatrifluoromethyl aniline: | 21.2% |
| paratrifluoromethyl aniline: | 2.1% |

This mixture is distilled as in Example 1. Four hundred ninety-eight g of orthotrifluoromethyl aniline at a concentration of more than 99% are obtained, which corresponds to a distillation yield of the orthotrifluoromethyl aniline of 97%.

EXAMPLE 3

Seven and three-tenths kg of trifluoromethyl benzene and 62.4 g of antimony are added to the reactor of Example 1. Chlorine is then added as in Example 1 at 20° C. for 3.5 hours. After washing with water, 9170 g of a mixture are obtained with the following analysis by vapor-phase chromatography:

| | |
|---|---|
| trifluoromethyl benzene: | 0.7% |
| metachlorotrifluoromethyl benzene: | 65.5% |
| parachlorotrifluoromethyl benzene: | 5.2% |
| orthochlorotrifluoromethyl benzene: | 1.5% |
| dichlorotrifluoromethyl benzenes: | 27.1% |

Conversion of the trifluoromethyl benzene is 99.1% and the overall yield is 97%.

Two thousand seven hundred fifty-three g of the preceding crude mixture are then added to an agitated reactor. The reactor contents are cooled to 10° C. and a mixture of fuming nitric acid (1700 g) and concentrated (97%) sulfuric acid (2350 g) is introduced under agitation at 10° C. over the course of one hour.

The mixture is then brought to 80° C. and held there for six hours. The organic phase is poured off and washed with water, 10% caustic soda, and then again with water. In this way, 3200 g of a mixture are collected with the following composition:

| | |
|---|---|
| chlorotrifluoromethyl benzene: | none detectable |
| nitrotrifluoromethyl benzene: | 0.7% |
| chloronitrotrifluoromethyl benzenes: | 72.9% |
| dichloronitrotrifluoromethyl benzenes: | 26.4% |

Conversion of the chlorotrifluoromethyl benzene is 100% and the overall yield is 94%.

Twenty-nine hundred ml of methanol and 50 g of Raney nickel doped with chromium are added to an agitated autoclave. The mixture is brought to 50° C. under 12 bars of hydrogen with agitation during a period of 15 minutes. Under these conditions, 1000 g of the nitration product previously obtained are added over the course of 1.75 hours. The mixture is maintained for an additional 1.5 hours at 50° C. under 12 bars of hydrogen with agitation. It is found that all of the chloronitrotrifluoromethyl benzenes have been consumed. Six hundred thirty g of 31.1% caustic soda are added and agitated at 50° C. under 12 bars of hydrogen for 15 minutes. Fifty g of Raney nickel are added and hydrogenation carried out for two hours at 50° C. under 12 bars of hydrogen. Another 50 g of Raney nickel are added and the hydrogenation continued for 3 hours under the same conditions. The reaction is then complete.

After filtration, concentration, and washing with water, 660 g of mixture obtained are with the following composition:

| | |
|---|---|
| orthotrifluoromethyl aniline: | 78.2% |
| metatrifluoromethyl aniline: | 19.7% |
| paratrifluoromethyl aniline: | 2.1% |

This mixture is distilled in the same manner as in Example 1. Five hundred five g of orthotrifluoromethyl aniline of a concentration of more than 99% are obtained, which corresponds to a distillation yield of orthotrifluoromethyl aniline of 98%.

Variations and modifications will be apparent to one skilled in the art and the claims are intended to cover all variations and modifications that fall within the true spirit and scope of the invention.

We claim:

1. A method of preparing orthotrifluoromethyl aniline from trifluoromethylbenzene, comprising the steps:
   (a) reacting the trifluoromethyl benzene with gaseous chlorine in the presence of a chlorination catalyst until at least 90% of the trifluoromethyl benzene is consumed, thereby forming a crude mixture containing chlorotrifluoromethyl benzenes;
   (b) nitrating the crude mixture from step (a) with a mixture of sulfuric and nitric acids until the chlorotrifluoromethyl benzenes are essentially completely consumed, thereby forming an organic phase containing chloronitrotrifluoromethyl benzenes;
   (c) decanting and washing the organic phase;
   (d) hydrogenating the organic phase from step (c) with a hydrogenation catalyst selected from the group consisting of Raney nickel and Raney nickel doped with chromium, in an organic solvent until the chloronitrotrifluoromethyl benzenes are essentially completely consumed;
   (e) hydrogenating the mixture from step (d) in the presence of an additional amount of hydrogenation catalyst and in the presence of alkali base, thereby forming a crude mixture containing orthotrifluoromethyl aniline; and
   (f) separating the orthotrifluoromethyl aniline from the crude mixture formed in step (e).

2. The method according to claim 1 wherein the chlorination catalyst is selected from the group consisting of ferric chloride, antimony pentachloride, iron, and antimony.

3. A method according to claim 2 wherein the chlorination catalyst is antimony pentachloride.

4. A method according to any of the preceding claims wherein the concentration of the chlorination catalyst in step (a) is from about 0.1 to about 10% by weight based on the trifluoromethyl benzene initially present.

5. A method according to claim 1 wherein step (a) is carried out at a temperature from about 0° to about 100° C. under atmospheric pressure.

6. A method according to claim 1 wherein step (a) is carried out until at least 95% of the trifluoromethyl benzene initially present has been consumed.

7. A method according to claim 1 wherein in step (b) the sulfuric acid and the nitric acid are used in such amounts that the weight ratio of each of them to the chlorotrifluoromethyl benzenes initially present in the nitration reaction medium is from about 0.5/1 to about 5/1.

8. A method according to claim 1 wherein step (b) is carried out at a temperature from about 0° to about 80° C. under atmospheric pressure.

9. A method according to claim 1 wherein in steps (d) and (e) a hydrogen pressure of from about 10 to about 50 bars is used.

10. A method according to claim 1 wherein the concentration of the hydrogenation catalyst in step (d) is about 3 to about 10% by weight based on the chloronitrotrifluoromethyl benzenes initially present.

11. A method according to claim 1 wherein in steps (d) and (e) the solvent is selected from the group consisting of methanol, ethanol, and propanol.

12. A method according to claim 11 wherein the solvent is methanol.

13. A method according to claim 1 wherein in steps (d) and (e) the temperature is from about 20° to about 100° C.

14. A method according to claim 1 wherein in step (e) the alkali base is selected from the group consisting of caustic soda and caustic potash.

15. A method according to claim 1 wherein in step (e) from about 8 to about 20% by weight of Raney nickel based on the chloronitrotrifluoromethyl benzenes initially present in step (d) is introduced in one or more portions.

* * * * *

UNITED STATES PATENT AND TRADEMARK OFFICE
CERTIFICATE OF CORRECTION

PATENT NO. : 4,387,246
DATED : June 7, 1983
INVENTOR(S) : Disdier et al.

It is certified that error appears in the above—identified patent and that said Letters Patent is hereby corrected as shown below:

At column 3, line 31, "chlorotrifluoromethyl" should be --chloronitrotrifluoromethyl--.

At column 4, line 41, delete "an".

At column 4, line 56, add a comma after "99%" (first occurrence).

At column 7, line 34, "The method" should be --A method--.

At column 8, lines 22-23, "(d) is about" should be --(d) is from about--.

Signed and Sealed this

Third Day of April 1984

[SEAL]

Attest:

Attesting Officer

GERALD J. MOSSINGHOFF

Commissioner of Patents and Trademarks